United States Patent [19]

Strohmaier

[11] Patent Number: 4,661,060
[45] Date of Patent: Apr. 28, 1987

[54] DENTAL HANDPIECE

[75] Inventor: Ernst Strohmaier, Schussenried, Fed. Rep. of Germany

[73] Assignee: Kaltenbach & Voigt GmbH & Co., Biberach/Riss, Fed. Rep. of Germany

[21] Appl. No.: 829,713

[22] Filed: Feb. 10, 1986

[30] Foreign Application Priority Data

Feb. 28, 1985 [DE] Fed. Rep. of Germany ....... 3507083

[51] Int. Cl.[4] .......................... A61C 1/10; A61C 1/12
[52] U.S. Cl. ..................................... 433/82; 433/131; 433/126
[58] Field of Search ..................... 433/131, 82, 84, 85, 433/126

[56] References Cited

U.S. PATENT DOCUMENTS

| 4,060,870 | 12/1977 | Cannarella | 433/131 |
| 4,315,741 | 2/1982 | Reichl | 433/82 |
| 4,619,614 | 10/1986 | Baba | 433/131 |

FOREIGN PATENT DOCUMENTS

| 1864407 | 8/1960 | Fed. Rep. of Germany . |
| 1250053 | 9/1967 | Fed. Rep. of Germany . |
| 3122065 | 3/1982 | Fed. Rep. of Germany . |
| 3215372 | 11/1983 | Fed. Rep. of Germany . |

Primary Examiner—Robert Peshock
Attorney, Agent, or Firm—Scully, Scott, Murphy & Presser

[57] ABSTRACT

A dental handpiece with a built-in electric motor for the drive of a dental treating implement which is arranged at one end of the handpiece. The implement is suppliable with a cooling medium through a cooling medium conduit in the handpiece; whereby the handpiece is detachably connectable with a current provider at its end which is distant from the implement, in which the current provider possesses electrical current supply contacts which are supplied with electrical current and which, upon the connection of the current provider with the handpiece, come into contact with current commutator or receiving contacts of the electric motor. The handpiece can be selectively supply-main or battery powered; in essence, unrestrictedly operated whereby, as a consequence of the cooling medium conduit which is fixed on the handpiece and the cooling medium supply conduit which is fixed on the at least one electrical current supply past, this automatically assures a concurrent secure and rapid separation and connection of the cooling medium conduit and cooling medium supply conduit upon the separation and connection of the handpiece and the current provider.

31 Claims, 13 Drawing Figures

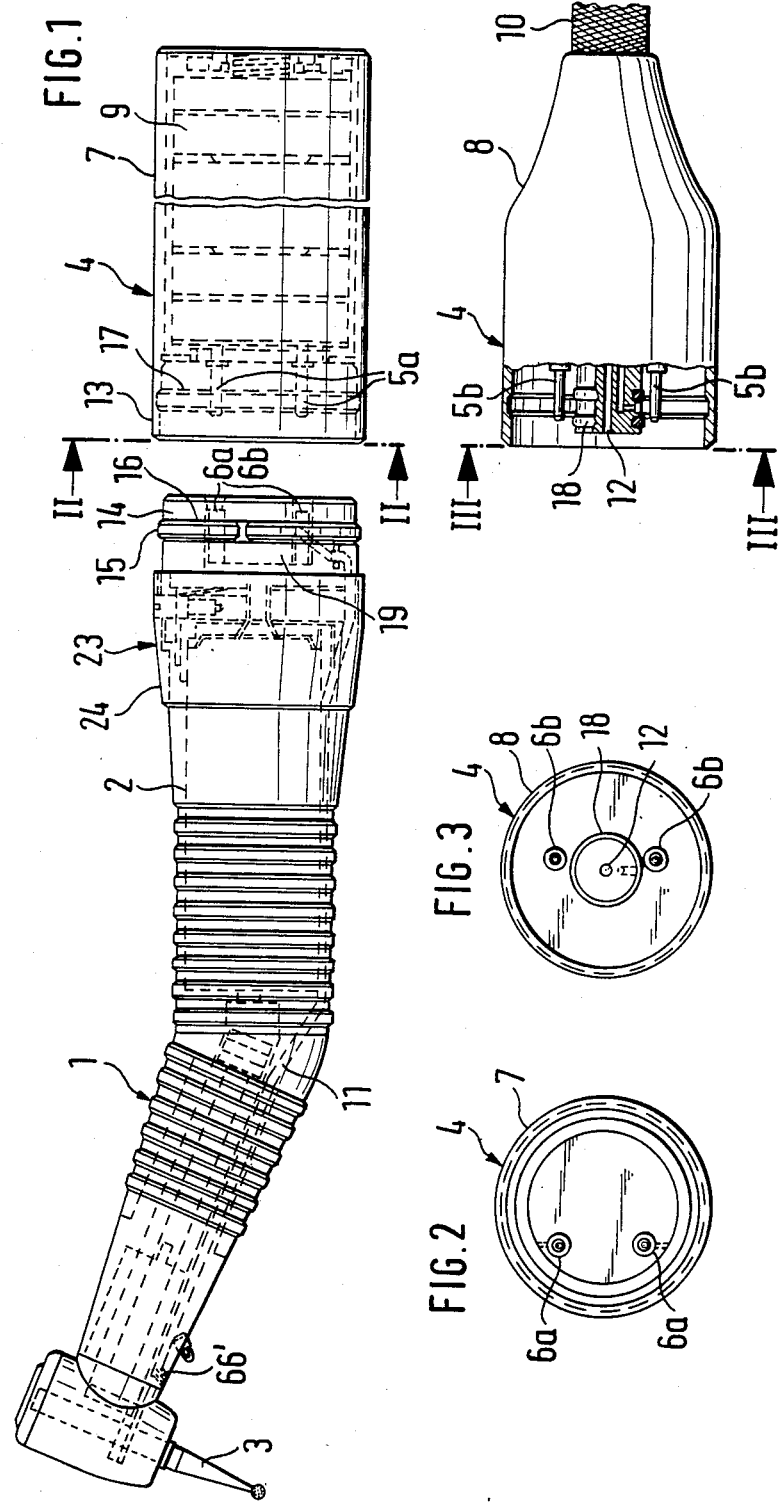

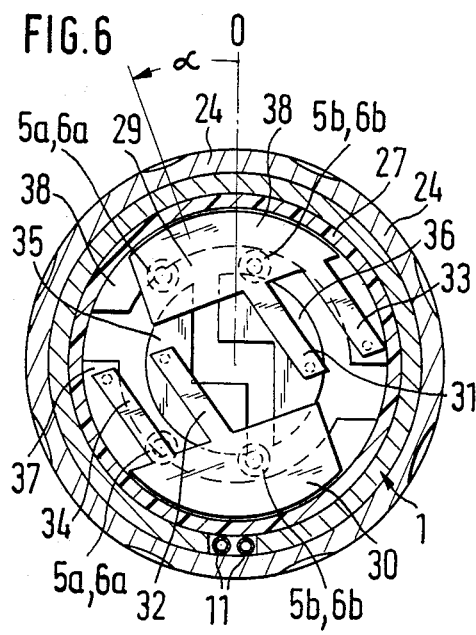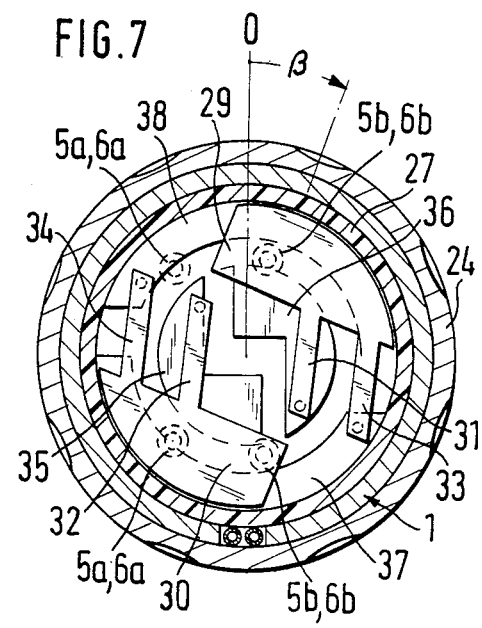

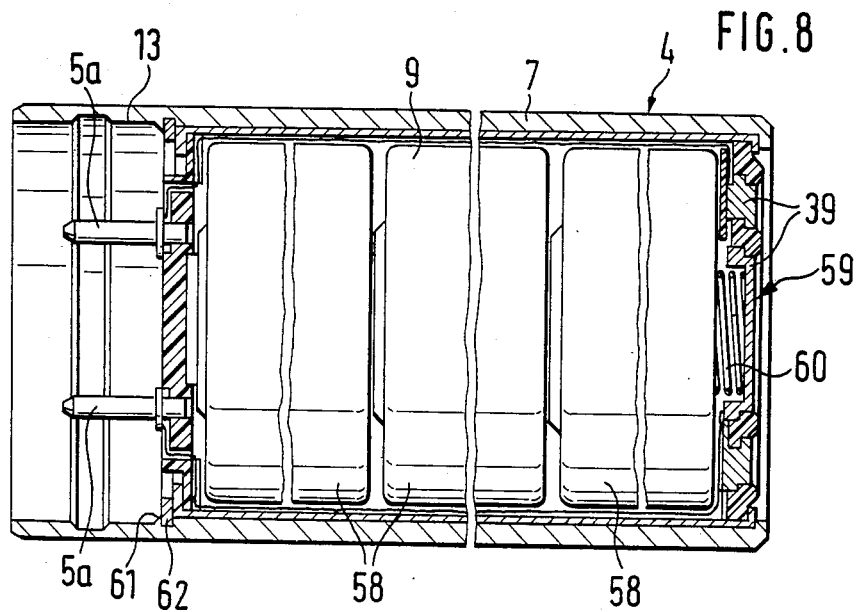
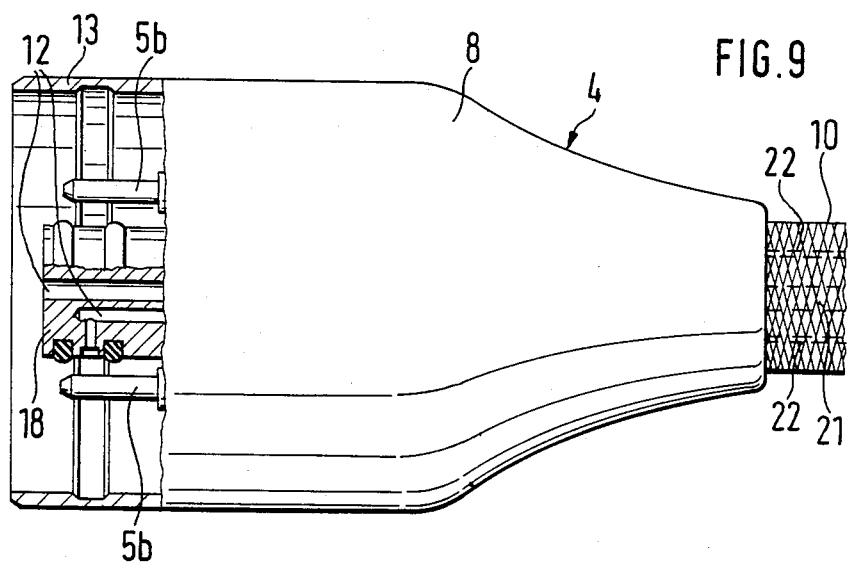

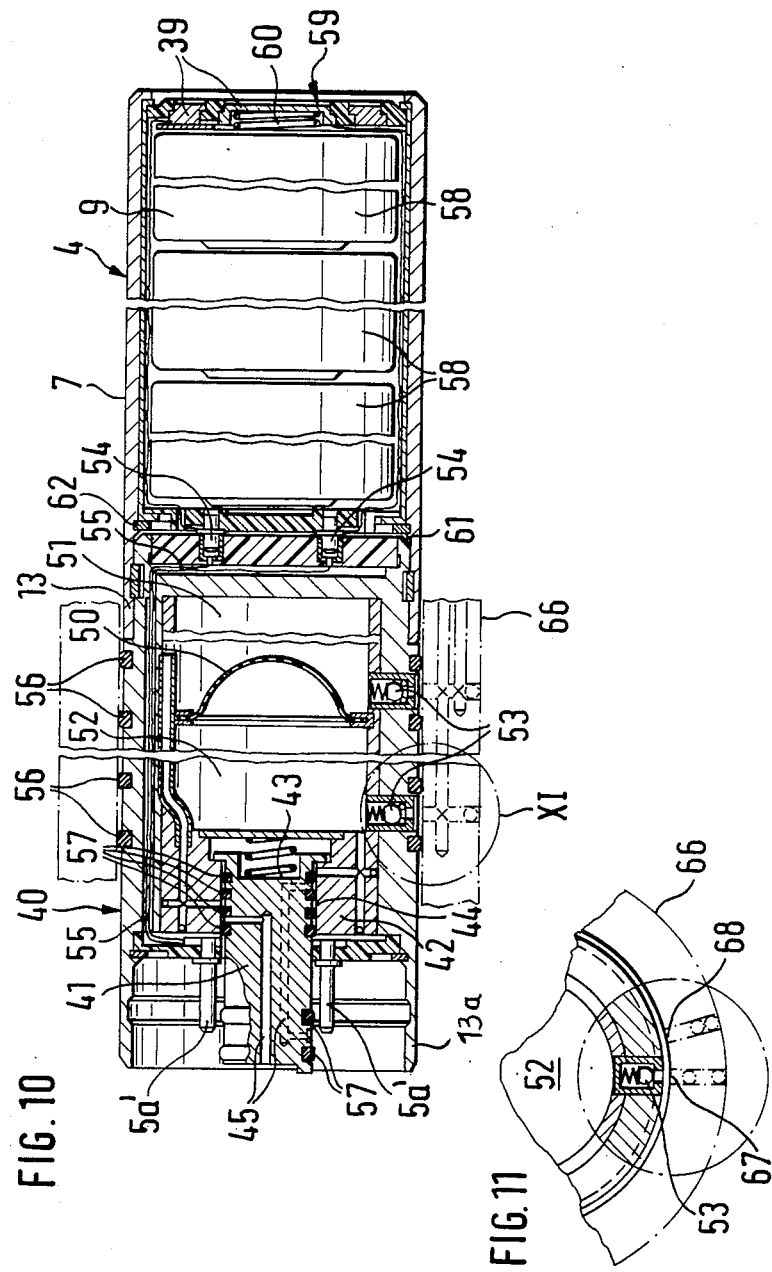

DENTAL HANDPIECE

BACKGROUND OF THE INVENTION

1. Field of the Invention

The present invention relates to a dental handpiece with a built-in electric motor for the drive of a dental treating implement which is arranged at one end of the handpiece. The implement is suppliable with a cooling medium through a cooling medium conduit in the handpiece; whereby the handpiece is detachably connectable with a current provider at its end which is distant from the implement, in which the current provider possesses electrical current supply contacts which are supplied with electrical current and which, upon the connection of the current provider with the handpiece, come into contact with current commutator or receiving contacts of the electric motor.

2. Discussion of the Prior Art

A handpiece of this type has become known from the disclosure of German Published Patent Appln. No. 12 50 053. In this presently known prior art handpiece, the current provider is equipped with a current supply cable, whereby a cooling medium supply conduit opens or discharges from the side of the current provider, and on whose discharging end there is attached a hose or tube forming the cooling medium conduit of the handpiece, and which extends exteriorly along the handpiece. Independently of the fact that this known handpiece can only be constantly employed in close proximity to a positionally fixed current supply source serving for supplying electrical current to the current supply cable; in general, only in a dental practice possessing a dental supply apparatus forming such an electrical current supply source, and as a consequence only utilizable in a restricted extent, because of the above-mentioned hose-plug connection it is not possible to effect a rapid automatic separation and connection of the cooling medium conduit of the handpiece and the cooling medium supply conduit of the current provider.

A handpiece which possesses to a different type of construction, and in which there lacks a cooling medium conduit in the handpiece, has become known from the disclosure of German Laid-Open Patent Appln. No. 31 22 065. In this known handpiece, the current supplier or provider consists of an input unit containing a battery. Besides the aspect that this known handpiece does not afford any capabilities for the cooling of the treating implement, also in this instance is there provided only a limited scope of utilization, inasmuch as any operation by means of a current provider other than a battery; for instance, an operation which in the given case would spare the battery, through a power supply apparatus supplied from electrical power mains and containing the positionally fixed electrical current supply source is, on the one hand, not possible because of the absence of a current provider adapted for this purpose, and on the other hand, because of the mentioned lack of cooling of the implement necessitated by the relatively high rotational speeds of the implement attainable during power-main supplied operation. In general, dental treatments require rotational speeds of the implement of 4,000 r.p.m. and, additionally, a constant cooling medium infeed to the tooth or the implement.

SUMMARY OF THE INVENTION

Accordingly, it is an object of the present invention to provide a dental handpiece of the above-mentioned type which is capable of an unrestricted operation; in essence, even an operation which is independent of a special dental, positionally fixed electrical current supply source, in effect also in operation outside of the dental practice, for example, in the home of the patient or in a hospital. However, in the case of a cooling of the implement which is contemplated at the especially high rotational speeds of the implement during power-main supplied operation, in which case the current provider possesses a cooling medium supply conduit, there is afforded a rapid automatic separation and connection of the cooling medium conduit of the handpiece and the cooling medium supply conduit of the current provider during the separation and connection of the handpiece and current provider.

The advantages which are achieved through the present invention can be essentially ascertained in that one and the same handpiece can be selectively supply-main or battery powered; in essence, unrestrictedly operated whereby, as a consequence of the cooling medium conduit which is fixed on the handpiece and the cooling medium supply conduit which is fixed on the at least one electrical current supply past, this automatically assures a concurrent secure and rapid separation and connection of the cooling medium conduit and cooling medium supply conduit upon the separation and connection of the handpiece and the current provider.

BRIEF DESCRIPTION OF THE DRAWINGS

Further advantageous embodiments and features of the invention can now be ascertained from the following detailed description thereof, taken in conjunction with the accompanying drawings; in which:

FIG. 1 illustrates a side view of a dental handpiece with the two differently constructed current supply parts associated with the handpiece and selectively connectable therewith;

FIG. 2 illustrates a sectional view taken along line II—II in FIG. 1;

FIG. 3 illustrates a sectional view taken along line III—III in Fig. 1;

FIG. 6 illustrates the switch device of FIG. 5 in the switched-on position for the clockwise rotation of the handpiece motor;

FIG. 7 illustrates the switch device of FIG. 5 in the switched-on position for the counter-clockwise rotation of the handpiece motor;

FIG. 8 illustrates a sectional view of a current supply part incorporating a battery;

FIG. 9 illustrates, partially in section and partially in side view of the current supply part incorporating an electrical current supply cable;

FIG. 10 illustrates a sectional view of the current supply part incorporating the battery with associated cooling medium supply receptacle;

FIG. 11 illustrates the detail XI shown encircled in FIG. 10 in a sectional view and on an enlarged scale;

DETAILED DESCRIPTION

Figure 5:
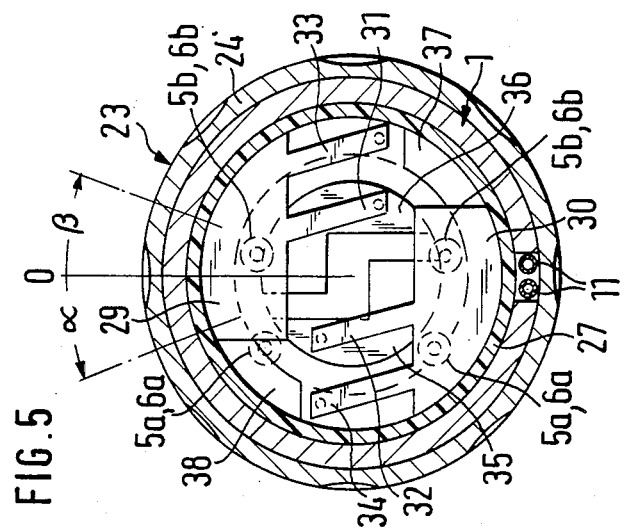
FIG. 5 illustrates a sectional view of a switch device for the handpiece shown in the switched-off position, taken along line V—V in FIG. 4.
Figure 4:
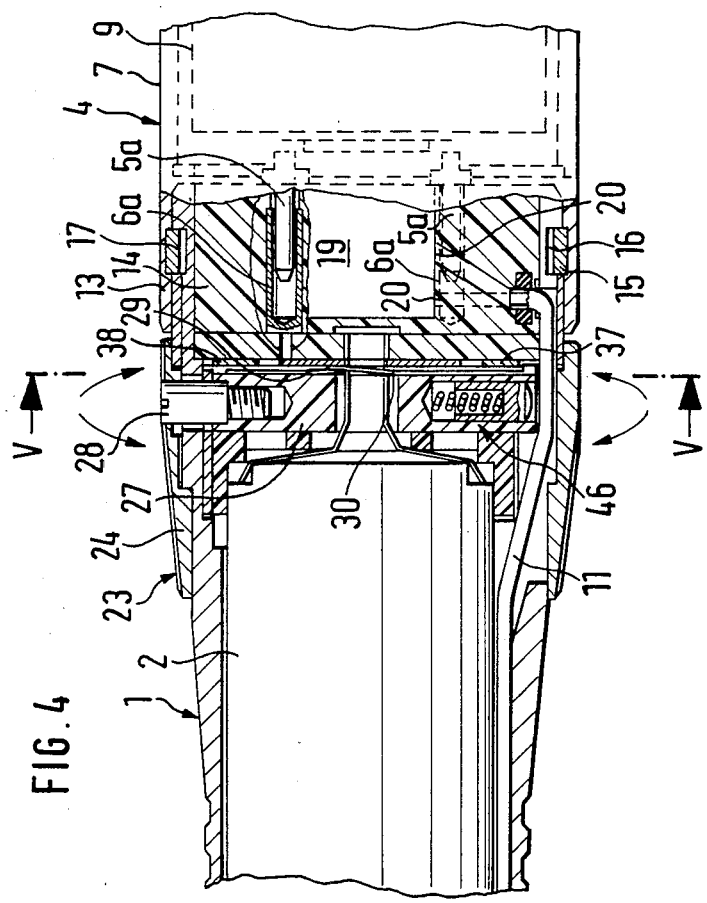
FIG. 4, in section, a partial segment of the handpiece in connection with the partly illustrated current supply part possessing a battery.

The dental handpiece 1 possesses a built-in electric motor 2 for the drive of a dental treating implement 3; for example, a drill, which is supported on one end of the handpiece, and which is suppliable with a cooling medium, for instance, water and/or air, through at least one cooling medium conduit 11 of the handpiece. The handpiece 1 is detachably connectable with a current supplier or provider 4 at the end which is remote from the implement, which possesses current infeed or supply contacts 5a, 5b which are supplied with electrical current, and which upon the connection of the current provider 4 with the handpiece 1 come into electrically conductive contact with current commutator or receiving contacts 6a, 6b of the electric motor 2.

As can be especially ascertained from FIG. 1, the current provider 2 encompasses two differently constructed current supply parts 7, 8 which are selectively connectable with the handpiece 1.

Each current supply part 7, 8 possesses current infeed or supply contacts 5a, 5b. The one current supply part 7 is equipped with a battery 9, and the other current supply part 8 with a flexible current supply cable 10 which leads to a supply source (not shown) for electrical current, for example, a current supply cable 10 leading to a dental unit or supply apparatus, for respectively supplying electrical current to the current supply contacts 5a, 5b. At least the current supply part 8 which is equipped with the current supply cable 10 possesses at least one cooling medium supply conduit 12 which, in the illustrated instance, extends within the interior of the current supply part, which upon connection of the current supply part 8 with the handpiece 1 comes concurrently automatically into connection with the cooling medium conduit 11 which is fixed on the handpiece 1, and in the illustrated embodiment extends within the handpiece.

As is particularly ascertainable from FIGS. 2 and 3, the current commutator or receiving contacts 6a provided for contacting with the current supply contacts 5a of the current supply part 7 incorporating the battery 9, and the current receiving contact 6b provided for contacting with the current supply contacts 5b of the current supply part 8 incorporating the current supply cable 10 are arranged separated from each other on the handpiece 1. In a corresponding manner are the current supply contacts 5a, 5b of the current supply parts 7, 8 arranged on these parts.

From the drawings there can be additionally ascertained that the current supply contacts 5a, 5b of the current supply parts 7, 8 are formed as socket plug pins and the current receiving contacts 6a, 6b of the handpiece 1 are formed as a plug socket receiving the socket plug pins. Hereby, the contacts 5a, 5b and 6a, 6b are arranged in the mutually facing end surfaces of the bushing-shaped current supply parts 7, 8 or the handpiece 1.

In order to further render easier the separation and above all the connection of the current supply parts and the handpiece, the current supply contacts 5a, 5b of the current supply parts 7, 8 are encompassed by a receiving sleeve 13 presently formed by an extension of the parts, into which there is insertable at a clamping fit, as a centering aid, a guide member 14 possessing the current receiving contacts 6a, 6b of the handpiece 1, and which is formed as an extension of the latter. For securing the connection, a clamping ring or collet 15 is arranged on the outer wall structure of the guide member 14, which comes into contact with the inner wall structure of the receiving sleeve 13. Hereby, the configuration is such that the collet 15 is arranged for axial positioning thereof in an external annular groove 16 formed in the guide member 14, whereby the receiving sleeve 13 possesses an internal annular groove 17 which receives the collet.

Figure 12:
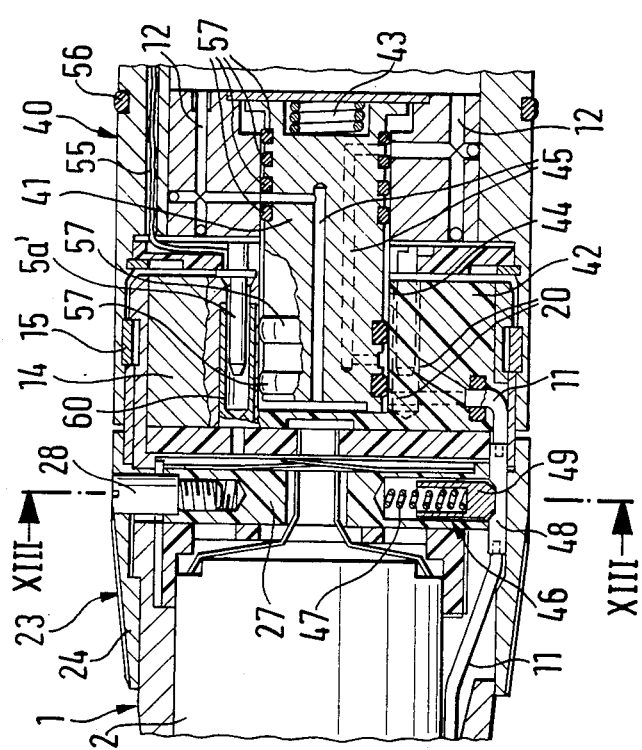
FIG. 12 illustrates a sectional view of the end of the cooling medium receptacle connected with the handpiece which is remote from the current supply part.

Furthermore, in order to render easier the separation and, especially, the connection between the current supply part and handpiece, pursuant to FIG. 12 the at least one cooling medium infeed conduit 12 of the current supply part 7 or 8 discharges from a guide trunnion 18 forming an extension of the last-mentioned part which, during connection with the handpiece 1, is introduceable into a receiving opening 19 of the handpiece, whereby intakes 20 are formed in the wall of the receiving opening 19 of the at least one cooling medium conduit 11 of the handpiece 1, for the transition of the cooling medium egressing from the cooling medium supply conduit 12.

As can be ascertained especially from FIG. 9, the current supply cable 10 is formed as a supply hose, additionally with electrical contact wires 22 which are connected with the current supply contacts 5b, and also containing a cooling medium supply conduit 21 which supplies the cooling medium infeed conduit 12 of the current supply part 8.

A switch device 23 is associated with the electric motor 2. Since, during the supply of the handpiece 1, or its electric motor 2 through the current supply part 8 possessing the current infeed cable 10, there is effected the regulation; for example, switching on and off, clockwise and counterclockwise rotation, by means of a dental unit apparatus, in effect a foot-actuated pedal or switch, as explained in further detail herein below in conjunction with FIGS. 5 through 7, the arrangement is such that the switch device 23, during the supply of the handpiece 1 through the current supply part 7 possessing the battery 9, is positioned in the current circuit supplying the electric motor, and is shunted over during the supply of the handpiece by the current supply part 8 possessing the current infeed cable 10.

The switch device 23 which is arranged on the handpiece 1 possesses a switching collar 24 which, as can be ascertained from FIGS. 5 through 7 and 13, is supported on the handpiece 1 so as to be rotatable from a middle null position 0 in both directions through an angle α or β each limited by a stop 25 into an operative position corresponding to either the clockwise or counterclockwise rotation of the electric motor 2. The stops are herein formed by the ends of a cutout 26 extending over a portion of the circumference of the wall of the handpiece 1, against which ends in the applicable operative position, there comes into contact a follower pin 28 of the switching collar 24, which extends through the cutout 26 and engages into a rotor which is 27 supported in the interior of the handpiece.

Pursuant to FIGS. 5 through 7 the construction of the switch device 23 is, in detail such that on the rotor 27 which is rotatable along by means of the switching collar 24, there are provided two contact members 29, 30 which stand in connection with the electric motor 2, each of which respectively possess two contacts springs 31, 32, 33, 34, whereby, presently, the one contact spring 31, 32, independently of the rotational position of the switching collar 24, is in constant electrical connection with one of two conductive paths 35, 36 electrically connected through the contact connection 5b, 6b during the connection of the handpiece 1 with the current supply part 8 possessing the current infeed cable 10; and whereby of the other two contact springs 33, 34, presently one in each of the two operative positions of the switching collar 24, can be brought into electrical connection with respectively one of two conductive paths 37, 38 which are electrically connected with a contact connection 5a, 6a produced during the connection of the handpiece 1 with the current supply part 7 possessing the battery 9.

For connection to a battery charger (not shown), pursuant to FIG. 10 the current supply part 7 possessing the battery 9 is equipped with charging contacts 39.

In order, if required, that even for a battery-operated electric motor 2 it be possible to effect a cooling of the implement 3 or the treating location on the tooth, the embodiment pursuant to FIGS. 10 and 12 is configured in such a manner that the current supply part 7 which possesses the battery 9 has a cooling medium supply receptacle 40 associated therewith, which possesses at least one cooling medium discharge conduit and which, upon the connection of the current supply part 7 with the handpiece 1, forms the at least one cooling medium infeed conduit 12 which is connectable with the last-mentioned cooling medium conduit 11. Pursuant to FIG. 12, the cooling medium supply receptacle 40 possesses a sliding guide trunnion 41 which, upon connection with the handpiece 1, is insertable into the receiving opening 19 of the handpiece, which is supported in a cutout 44 provided in a thickened end wall 42 of the cooling medium supply container 40 in such a manner that, upon connection with the handpiece, it is movable against the action of a resetting member 43 in a direction towards the interior of the receptacle 40, and upon detachment from the handpiece is moved back under the action of the return member 43, such that upon connection with the handpiece 1, there is opened the inlet from the cooling medium infeed conduit 12 and, thereby, the inlet into the cooling medium conduit 11 of the handpiece is opened, and is closed off upon the detachment of the handpiece from the above-mentioned outlet. Hereby, the sliding guide trunnion 41 is provided with at least one cooling medium connecting conduit 45 extending therethrough and forming the cooling medium outlet conduit which, upon connection with the handpiece 1, contacts the at least one cooling medium infeed conduit 12 with the cooling medium conduit 11 of the handpiece 1. The transitions between the above-mentioned conduits 12, 45, 11 are sealed through the use of sealing rings 57 surrounding the sliding guide trunnion 41.

Figure 13:
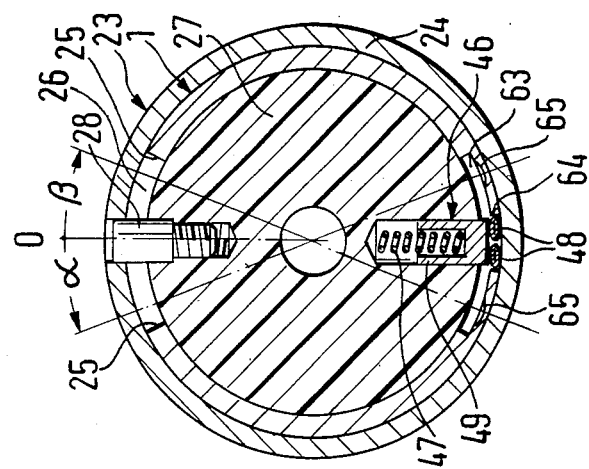
FIG. 13 illustrates a sectional view taken along line XIII—XIII in FIG. 12.

In the embodiment pursuant to FIGS. 12 and 13, the cooling medium conduit 11 of the handpiece 1 has a shutoff valve 46 associated therewith, which is coupled in such a manner with the switch device 23 which is associated with electric motor 2, that upon the electric motor being switched off, the valve will close off the cooling medium conduit 11 and with a switched-on electric motor will open the cooling medium conduit. Hereby, the shutoff valve 46 consists of a clamping bolt 49, which squeezes shut an elastic section 48 of the at least one cooling medium conduit 11 under the action of a resetting member 47, and which clamping bolt is rotatable together with the switching collar 24. As can be ascertained especially from FIG. 13, the elastic cooling medium conduit section 48 is arranged in a recess 64 provided in depression of the inner wall of the sleeve-shaped handpiece 1. At both ends of the depression 63 there is provided a latching detent 65 for the clamping bolt 49, each of which, respectively, correspond to one of the two end switching positions of the switching collar 24.

As is further illustrated in FIGS. 12 and 13, the clamping bolt 49 is supported in the rotor 27 which is connected with the switching collar 24.

From FIG. 10 there can be ascertained that the interior space of the cooling medium supply receptacle 40 is divided by means of a membrane 50 into two cooling medium supply chambers; in effect, an air tank 51 and a water tank 52, from each of which there respectively exits a separate cooling medium infeed conduit 12. Hereby, the tanks 51, 52 are filled in such a manner that the membrane 50 will deflect into the water tank 52. In this manner, both cooling media, in effect, air and water, at a tensioned or compressed resetting member 43 which is suitably formed by a coiled compression spring, will be dispensed under pressure from the cooling medium discharge opening 66' of the handpiece 1 (FIG. 1). The tensioning or compressing of the resetting member 43 is carried out at the attachment of the handpiece 1 to the cooling medium receptacle 40 pursuant to FIG. 12.

As can be ascertained from FIG. 10, the cooling medium receptacle 40 possesses two cooling media-refill valves 53 and, in essence, the air tank 51 as well as the water tank 52 are each provided with a cooling media-refill valve 53. Each refill valve 53 is arranged in the wall of the cooling medium receptacle 40 intermediate two axially spaced sealing rings 56 encompassing the receptacle 40. The cooling mediarefill valve 53 serve for the refilling of water or air with the aid of a filling jacket 66 as illustrated in FIGS. 10 and 11, which, in cooperation with the sealing rings 56, is slid onto the cooling medium receptacle 40 in such a manner that cooling medium discharge openings 67 or 68 of the filling jacket 66 are positioned opposite the refill valves 53 which are constituted of nonreturn valves, and thereafter carried out effected the refilling procedure.

From FIG. 10 there is further ascertainable that the cooling medium supply receptacle 40 is connected with the current supply part 7 possessing the battery 9 through the intermediary of an electric socket plug connection 54, whereby electrical connecting cables 55 leading from the socket plug connection 54, upon connection of the cooling medium receptacle 40 with the handpiece 1 coming into contact with the current receiving contacts 6a of the handpiece 1, are conducted to current infeed contacts 5a' located on the cooling medium receptacle 40. The detachable socket plug connection 54 between the cooling medium receptacle 40 and the current supply part 7 is constructed similar to the above-mentioned detachable socket plug connection between the current supply part 7 or 8 and the handpiece 1. The connecting cables 55 are arranged in the wall of the cooling medium receptacle 40. The current infeed contacts 5a' are constructed, as are the contacts 5a, as socket pins. The cooling medium receptacle 40 possesses a sleeve extension 13a for the receipt of the guide member 14 of the handpiece 1 which is constructed as a plug extension.

As is illustrated in FIGS. 8 and 10, the battery 9 consists of a plurality of adjoiningly arranged individual cells 58, which are retained in electrical contact by a resetting member 60 on the bottom 59 of the cup-shaped current supply part 7, and are secured in the current supply part 7 through a spring ring 62 supported against an internal collar 61 of the current supply part 7. The resetting member 60 is formed by a coiled compression spring.

What is claimed is:

1. In a dental handpiece including a built-in electric motor for the drive of a dental treating implement mounted at one end of the handpiece, a cooling medium conduit on said handpiece for supplying said implement with a cooling medium; a current provider detachably connectable to the end of the handpiece which is remote from the implement, said current provider including current infeed contacts supplied with electrical current, said contacts coming into contact with current receiving contacts of the electric motor upon connection of the current provider with the handpiece; the improvement comprising: said current provider consisting of two differently constructed current supply parts which are selectively connectable with the handpiece, each said current supply part having current supply contacts, one said current supply part possessing an electric battery and the other said current supply part possessing a current supply cable for respectively supplying electrical current to the current supply contacts, and wherein at least the current supply part possessing the current supply cable includes at least one cooling medium infeed conduit arranged on said current supply part which, upon the connection of the current supply part with the handpiece, concurrently comes into connection with said at least one cooling medium conduit on said handpiece.

2. A handpiece as claimed in claim 1, wherein the current receiving contacts for contact with the current supply contacts of the current supply part possessing the battery, and the current receiving contacts for contact with the current supply contacts of the current supply part possessing the current supply cable are arranged separated from each other on said handpiece.

3. A handpiece as claimed in claim 1, wherein said two current supply parts are sleeve-shaped in configuration.

4. A handpiece as claimed in claims 1, wherein the current supply contacts of said current supply parts comprise socket plugs and the current receiving contacts of the handpiece comprise plug sockets for receiving the socket plugs.

5. A handpiece as claimed in claims 1, wherein the current supply contacts of said current supply parts are each respectively encompassed by a receiving sleeve forming an extension of said parts, into which there are clamp-fittedly insertable the current receiving contacts of said handpiece on a guide member forming an extension of the handpiece.

6. A handpiece as claimed in claim 5, wherein a collet is mounted on the outer wall of said guide member which comes into contact with the inner wall of the receiving sleeve.

7. A handpiece as claimed in claim 6, wherein the collet is arranged in an external annular groove in the guide member for axial positioning thereof, said receiving sleeve possessing an internal annular groove for receiving said collet.

8. A handpiece as claimed in claim 1, wherein said at least one cooling medium infeed conduit of the current supply part discharges from a guide trunnion forming an extension of said part, which is insertable into a receiving opening in the handpiece during connection with the handpiece, and inlets being formed in the wall of the receiving opening of the at least one cooling medium conduit of the handpiece for the transition of the cooling medium egressing from the cooling medium infeed conduit.

9. A handpiece as claimed in claims 1, wherein said current supply cable comprises a supply hose, which contains a cooling medium supply conduit for supplying the cooling medium infeed conduit of one said current supply part.

10. A handpiece as claimed in claims 1, wherein switch means is associated with said electric motor.

11. A handpiece as claimed in claim 10, wherein said switch means is located in the current circuit supplying the electric motor during electrically supplying of the handpiece by the current supply part possessing the battery, and is shunted during the supplying of the handpiece by the current supply part possessing the current supply cable.

12. A handpiece as claimed in claim 10, wherein said switch means comprises a rotatable switching collar.

13. A handpiece as claimed in claim 12, wherein the switching collar is rotatably supported on the handpiece and is rotatable in both directions from an intermediate null position through an angle limited by a stop means into operative position corresponding to the clockwise or the counterclockwise rotation of said electric motor.

14. A handpiece as claimed in claim 13, wherein the stop means are formed by the ends of a cutout extending over a portion of the circumference of the wall of said handpiece, a follower pin on said switching coming into contact therewith in the applicable operative position, said follower pin extending through said cutout and engages into a rotor which is supported within the handpiece.

15. A handpiece as claimed in claims 10, wherein said switch means is arranged on said handpiece.

16. A handpiece as claimed in claim 12, wherein contact members are arranged on the switching collar which are in communication with the electric motor, each said member possessing two contact springs of which presently one contact spring, independently of the rotational position of the switching collar is in constant contact with presently one of two conductive paths electrically connected through the contact connection produced in the connection of the handpiece with the current supply part possessing the current supply cable, and wherein of the two other contact springs presently one spring in each of the two operative positions of the switching collar is positionable in electrical connection with conductive paths which are electrically connected formed by the contact connection upon connection of the handpiece with the current supply part possessing the battery.

17. A handpiece as claimed in claim 1, wherein said current supply part possessing the battery includes battery-charging contacts.

18. A handpiece as claimed in claim 1, wherein a cooling medium supply receptacle is associated with the current supply part possessing the battery, said receptacle having at least one cooling medium discharge conduit which, upon connection of said current supply part with the handpiece, forms said at least one medium infeed conduit which is connectable with the cooling medium conduit of the handpiece.

19. A handpiece as claimed in claim 18, wherein the cooling medium supply receptacle includes a sliding guide trunnion which is introduceable into the receiving opening of the handpiece upon connection with the handpiece, said trunnion being supported in a breakthrough of a thickened end wall of the cooling medium supply receptacle such as to be movable, upon connection with the handpiece, opposite the effect of a resetting element in a direction towards the interior of the receptacle and, upon detachment of the handpiece, is movable back under the action of said resetting element whereby, upon connection of the handpiece, the discharge from the cooling medium inlet conduit and the inlet to the cooling medium conduit of the handpiece is opened, and the discharge is blocked upon the detachment of the handpiece.

20. A handpiece as claimed in claim 19, wherein the sliding guide trunnion includes at least one cooling medium connecting conduit extending therethrough and forming the cooling medium discharge conduit which, upon connection with the handpiece, is connectable with said at least one cooling medium conduit of the handpiece.

21. A handpiece as claimed in claim 20, wherein the transitions between said conduit are sealed by sealing rings surrounding the sliding guide trunnion.

22. A handpiece as claimed in claim 1, wherein the cooling medium conduit of said handpiece has a shutoff valve operatively associated therewith.

23. A handpiece as claimed in claim 22, wherein said shutoff valve is operatively coupled to the switch means associated with the electric motor as to block the cooling medium conduit when the electric motor is switched off and to open the cooling medium conduit when the electric motor is switched on.

24. A handpiece as claimed in claim 23, wherein the shutoff valve comprises a clamping bolt squeezing an elastic section of said at least one cooling medium conduit under the action of a resetting element, said clamping bolt being rotatable in conjunction with the switching collar.

25. A handpiece as claimed in claim 24, wherein said clamping bolt is supported in the rotor which is connected to the switching collar.

26. A handpiece as claimed in claim 18, wherein the interior of said cooling medium supply receptacle is divided by a membrane into two cooling medium supply chambers, respectively, an air tank and a water tank; and a separate cooling medium supply conduit leading from each said chamber.

27. A handpiece as claimed in claim 18, wherein said cooling medium supply receptacle includes at least one cooling medium refill valve.

28. A handpiece as claimed in claim 26, wherein said air tank and said water tank are each equipped with a cooling medium refill valve.

29. A handpiece as claimed in claim 27, wherein said at least one cooling medium refill valve is arranged in the wall of the cooling medium receptacle intermediate two sealing rings surrounding said receptacle.

30. A handpiece as claimed in claim 19, wherein said cooling medium supply receptacle is connected with the current supply part possessing the battery through an electrical plug connection, electrical connecting cables extending from the plug connection whereby, during connection between the cooling medium receptacle and the handpiece, coming into contact with the current receiving contacts of the handpiece, the cables are conducted to the current supply contacts provided on the cooling medium receptacle.

31. A handpiece as claimed in claim 1, wherein the battery comprises a plurality of adjoiningly arranged individual cells which are retained in electrical connection through a resetting element located on the bottom of the cup-shaped current supply part possessing the battery, and secured by a spring ring supported against an internal collar in the current supply part.

* * * * *